(12) United States Patent
Brees et al.

(10) Patent No.: US 7,968,291 B2
(45) Date of Patent: Jun. 28, 2011

(54) RNA BIOASSAY

(75) Inventors: Dominique J. Brees, Ledyard, CT (US); James K. Loy, Gales Ferry, CT (US)

(73) Assignee: The Hamner Institute for Health Sciences, Research Triangle Park, NC (US)

( * ) Notice: Subject to any disclaimer, the term of this patent is extended or adjusted under 35 U.S.C. 154(b) by 533 days.

(21) Appl. No.: 11/960,093

(22) Filed: Dec. 19, 2007

(65) Prior Publication Data

US 2009/0004655 A1 Jan. 1, 2009

Related U.S. Application Data

(62) Division of application No. 10/745,823, filed on Dec. 24, 2003, now abandoned.

(60) Provisional application No. 60/437,533, filed on Dec. 31, 2002.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......... 435/6; 435/91.2; 536/23.1; 536/24.3
(58) Field of Classification Search .................. None
See application file for complete search history.

(56) References Cited

FOREIGN PATENT DOCUMENTS
GB 2364244 1/2002

OTHER PUBLICATIONS

Aranega, A.E. et al., Int. J. Cardiol., vol. 38, pp. 49-55 (1993).*
Aranega, A.E. et al., J. Mol. Cell Cardiol., vol. 25, pp. 15-22 (1993).*
Martinez-Amat et al., Br. J. Sports Med., vol. 39, pp. 830-834 (2005).*
Tsui, N.B.Y. et al., Clin. Chem., vol. 48, pp. 1647-1653 (Oct. 2002).*
Hasselmann, D.O. et al., Clin. Chem., vol. 47, pp. 1488-1489 (Aug. 2001).*
Yang, Y. et al., J. Clin. Investig., vol. 106, pp. 1321-1330 (2000).*
Funaki, N. O. et al., British Journal of Cancer, vol. 77, No. 8, pp. 1372-1332, 1996. "Cytokeratin 20 mRNA in Peripheral Venous Blood of Colorectal Carcinoma Patients".

* cited by examiner

*Primary Examiner* — Teresa E Strzelecka
(74) *Attorney, Agent, or Firm* — Myers Bigel Sibley & Sajovec PA

(57) ABSTRACT

The present invention relates to methods for evaluating the cell damaging potential of an agent by determining the ability of the agent to increase messenger RNA release in cells.

10 Claims, No Drawings

RNA BIOASSAY

CROSS REFERENCE TO RELATED APPLICATION

This application claims the benefit of U.S. Provisional Application No. 60/437,533 filed Dec. 31, 2002 and is a divisional application of U.S. patent application Ser. No. 10/745,823 filed Dec. 24, 2003, now abandoned.

FIELD OF THE INVENTION

The present invention relates to methods for evaluating the cell damaging potential of an agent by determining the ability of the agent to increase messenger RNA release in cells.

BACKGROUND OF THE INVENTION

In the pharmaceutical field, great efforts are being made to minimize the toxicological potential of pharmaceutical agents. Among the risks associated with exposure to toxic agents is the possibility of causing injury or death to cells of the body, which can result in damage to vital organs.

Mandel and Metais (1948) reported the discovery of extracellular nucleic acids in human plasma.

Lo, K. W. et al. (1990) and Kopreski, M. et al. (1999) have both reported the detection of tumor derived RNA in the plasma of cancer patients.

Chen, X. Q. et al. (2000) have proposed the use of telomerase RNA as a detection marker in the serum of breast cancer patients.

Poon, L. L. et al. (2000) have reported the presence of fetal RNA in maternal plasma.

U.S. Pat. No. 6,329,179 discloses the use of tumor-derived or associated extracellular RNA found circulating in the plasma or serum fraction of blood for the detection, monitoring, or evaluation of cancer or pre-malignant conditions.

U.S. Pat. No. 6,156,504 discloses the detection, identification, or monitoring of the existence, progression or clinical status of benign, pre-malignant, or malignant neoplasms in humans or animals that contain a mutation associated with the neoplasm through detection of the mutated nucleic acid of the neoplasm in plasma or serum fractions.

U.S. Pat. No. 6,020,124 discloses the detection of soluble DNA for mutated genes and oncogenes in biological fluids.

As RNA is considered to be labile, researchers have examined possible mechanisms by which RNA in human plasma is protected from degradation. Hasselmann, D. O. et al. (2001) have reported that in an in vitro model, mRNA within apoptotic bodies released by melanoma cells was protected from degradation when incubated in human serum.

Ng, E. K. O. et al. (2002) have reported that a substantial portion of plasma mRNA is particle-associated.

Tsui, N. B. Y., et al (2002) have examined the stability of endogenous and added RNA in blood, serum and plasma.

Conventional methods available for determining whether an agent causes tissue and cell damage include biochemical methods that measure markers of cell damage. For example, the enzymes, ALT, AST and 5'NT may be used as indicators of damage to liver cells (Duncan, J. R. et al. (1994). These enzymes, which are normally found in liver cells, are released when liver cells are damaged and may then be detected in the blood. However, the ability to use such indicators for early detection depends upon a number of factors, including the rapidity of enzyme release and the sensitivity of detection. Traditional methods are thus relatively insensitive and non-specific. Hence, there exists a growing interest to uncover additional early biological indicators or biomarkers of toxicity.

SUMMARY OF THE INVENTION

One aspect of this invention provides methods for evaluating an agent comprising treating one or more cells with an agent and measuring the effect of the agent on the amount of RNA released by the cells. In one embodiment of this aspect, the method further comprises characterizing the agent as an agent that is likely to cause cell injury, wherein the injury is characterized by increased RNA release, provided the amount of RNA released by the cells has increased. In another embodiment of this aspect of the invention, the cells comprise one or more cells of mammalian origin, preferably of human origin.

Another aspect of this invention provides methods for evaluating the cell-protective characteristics of an agent comprising: treating one or more cells with a first agent that causes cell injury, wherein the injury is characterized by increased RNA release from the injured cells; treating the cell with a second agent; and measuring the effect of the second agent in reducing the amount of RNA release by the cells that is caused by the first agent. In one embodiment of this aspect of the invention, the method further comprises characterizing the second agent as an agent that is likely to protect the cells from cell injury by a cell injury causing agent, wherein the cell injury is characterized by increased RNA release, provided the amount of RNA released by the cells has increased. In another embodiment of this aspect of the invention, the cells comprise one or more cells of mammalian origin, preferably of human origin.

An additional aspect of this invention provides methods of evaluating the effect of an agent on a subject comprising treating a subject with an agent; and measuring the effect of the treatment in increasing release into the blood of one or more RNA markers.

In one embodiment of the methods of this invention, the measurement of the effects on RNA release comprises measuring the effect of the agent on the quantity of one or more RNA markers.

In another embodiment of the invention, the measurement of levels of RNA release comprises RT-PCR.

In a further embodiment of the methods of the invention, the RNA markers are selected from albumin, cardiac actin, troponin T, SM22, smooth muscle actin, kidney androgen specific protein, Tamm-Horsfall protein and aquaporin-2.

In yet another embodiment of the methods of this invention comprising treating one or more cells with an agent, the cells are of mammalian liver, heart, smooth muscle or kidney origin.

DEFINITIONS

The terms used herein have their usual meaning in the art. However, to even further clarify the present invention and for convenience, the meaning of certain terms and phrases employed in the specification, including the examples and appended claims are provided below.

"Agent" means a chemical, biological or physical means for producing an effect. An agent may be one or a combination of two or more chemical or biochemical substances, biological pathogens or physical perturbations.

"Albumin" means a protein expressed in the liver, or whose corresponding mRNA is expressed in the liver, that is encoded by a nucleotide sequence having a nucleotide identity of 70% or greater to the nucleotide sequence of accession number BC034026.1 (SEQ ID NO:1), and which includes the albumin nucleotide sequences having the accession numbers provided below.

"Aquaporin-2" means a protein expressed in the kidney, or whose corresponding mRNA is expressed in the kidney, that is encoded by a nucleotide sequence having a nucleotide identity of 70% or greater to the nucleotide sequence of accession number AF147093.2 (SEQ ID NO:2), and which includes the aquaporin-2 nucleotide sequences having the accession numbers provided below.

"Cardiac actin" means a protein expressed in the heart, or whose corresponding mRNA is expressed in the heart, that is encoded by a nucleotide sequence having a nucleotide identity of 70% or greater to the nucleotide sequence of accession number J00071.1 (SEQ ID NO3), and which includes the cardiac actin nucleotide sequences having the accession numbers provided below.

"Kidney androgen specific protein" means a protein expressed in the kidney, or whose corresponding mRNA is expressed in the kidney, that is encoded by a nucleotide sequence having a nucleotide identity of 70% or greater to the nucleotide sequence of accession number U25808.1 (SEQ ID NO:4).

"Nucleotide identity" means the sequence alignment of a nucleotide sequence calculated against another nucleotide sequence, e.g. the nucleotide sequence of human megalin. Specifically, the term refers to the percentage of residue matches between at least two nucleotide sequences aligned using the standardized CLUSTAL W algorithm. This algorithm may insert gaps in the sequences being compared in a standardized and reproducible manner in order to optimize alignment between the sequences, thereby achieving a more meaningful comparison. Percent identity between nucleotide sequences is preferably determined using the default parameters of the CLUSTAL W algorithm as incorporated into the version 5 of the MEGALIGN™ sequence alignment program. This program is part of the LASERGENE™ suite of molecular biological analysis programs (DNASTAR, Madison Wis.). CLUSTAL W is described in Thompson 1994).

"Nucleotide sequence" and "polynucleotide" means DNA or RNA, whether in single-stranded or double-stranded form. The term "complimentary nucleotide sequence" means a nucleotide sequence that anneals (binds) to a another nucleotide sequence according to the pairing of a guanidine nucleotide (G) with a cytidine nucleotide (C) and adenosine nucleotide (A) with thymidine nucleotide (T), except in RNA where a T is replaced with a uridine nucleotide (U) so that U binds with A.

"Pathological state" means a state of biological abnormality and includes abnormal states of an organ, tissue type or cell type. The term includes abnormality regardless of the cause, and may include diseases, arising, for example, from physiological abnormalities, a genetic abnormalities or pathogenic agents, physical injuries, or toxicities caused by xenobiotic agents.

"Release" means to permit to escape, to excrete or to expel, whether by active or passive means.

"RNA marker" means an RNA polynucleotide, or a fragment thereof, having a specific sequence that is transcribed from the DNA genetic information of a cell. The term RNA marker includes mRNA polynucleotides, or fragments thereof, that have been processed by a cell, for example, by 5' capping, RNA splicing and 3' polyadenylation, following copying from the corresponding DNA sequence. When "RNA marker" is preceded by the name of an organ, tissue type or cell type (e.g., "liver RNA marker"), the term means that the RNA marker is transcribed in that organ, tissue type or cell type. For the purposes of this invention, such use of the term would preferably refer to RNA markers which are transcribed only in the designated organ, tissue type or cell type. However, the term also includes an RNA marker that can be used to identify the particular organ, tissue type or cell type of interest within the context of the invention. For example, in the methods of this that involve characterizing a pathological state of the liver by measuring a liver RNA marker in blood, the particular RNA marker does not have to be one exclusively expressed in liver, provided any expression, for example, in a second organ or tissue, is unlikely to be detected in blood as a result of pathology of that second organ or tissue.

"SM22" means a protein expressed in the smooth muscle, or whose corresponding mRNA is expressed in the smooth muscle, that is encoded by a nucleotide sequence having a nucleotide identify of 70% or greater to the nucleotide sequence of accession number D17409.1 (SEQ ID NO:5), and which includes the SM22 nucleotide sequences having the accession numbers listed in provided below.

"Troponin T" means a protein expressed in the heart, or whose corresponding mRNA is expressed in the heart that is encoded by a nucleotide sequence having a nucleotide identity of 70% or greater to the nucleotide sequence of accession number X83743.1, and which includes the troponin T nucleotide sequences having the accession numbers provided below.

"Tamm-Horsfall protein" means a protein expressed in the kidney, or whose corresponding mRNA is expressed in the kidney, that is encoded by a nucleotide sequence having a nucleotide identity of 70% or greater to the nucleotide sequence of accession number M15881.1 (SEQ ID NO:6), and which includes the Tamm-Horsfall protein nucleotide sequences having the accession numbers listed in provided below.

Abbreviations:

The abbreviations used herein have their usual meaning in the art. However, to even further clarify the present invention, for convenience, the meaning of certain abbreviations are provided as follows: "° C." means degrees centigrade; "5'NT" means 5-nucleotidase; "µl" means microliter; "ALT" means alanine aminotransferase; "AST" means aspartate transferase; "ATCC" means the American Type Tissue Culture Collection located in Manassas, Va. (website at www.atc.org); "cDNA" means complementary DNA; "dL" means deciliter, "DNA" means deoxyribonucleic acid; "EDTA" means ethylenediamine tetra-acetic acid; "EGTA" means ethylene glycol-bis(b-aminoethylether)-N,N,N',N'-tetraacetic acid; "FBS" means fetal bovine serum; "g" means gram; "$H_2O_2$" means hydrogen peroxide; "LDH" means lactate dehydrogenase; "kg" means kilogram; "NaOH" means sodium hydroxide; "MEM" means Modified Eagle's Medium; "mRNA" means messenger RNA; "mg" means milligram; "mL" means milliliter; "ng" means nanogram; "PCR" means polymerase chain reaction; "PBS" means phosphate buffered saline; "RNA" means ribonucleic acid; "RPM" means revolutions per minute; and "RT-PCR" means reverse transcriptase polymerase chain reaction.

DETAILED DESCRIPTION OF THE INVENTION

During normal cell turnover, mammalian cells release RNA that is detectable in the plasma. This invention is based, in part, on the discovery that the release of RNA by cells is exacerbated by cellular injury caused by chemical agents, and that this effect is a useful indicator of cell injury. One aspect of this invention makes use of the tissue-type specific and cell-type specific nature of gene transcription (i.e., that some genes may be transcribed and others may not) and the tissue-type and cell-type specific splicing arrangement of certain gene transcripts. RNAs that are distinctive of a particular tissue-type or cell-type may be used as biomarkers of biological, physiological or toxicological injury for specific organs, tissues or cell types.

The invention provides both in vivo and in vitro testing of potentially toxic agents, identification of therapeutic agents, and testing the efficacy of therapeutic agents, based upon the release of RNA by cells as an indicator of cell injury or cell death. RNA detection techniques known to those skilled in the art or that will be apparent based upon this disclosure are useful in the practice of this invention.

One embodiment provides in vitro methods for evaluating the cell damaging potential of an agent. According to these methods, cells or tissue cultures are exposed to one or more potentially toxic test agents. The release of RNA is then detected in the liquid medium surrounding the cells. The toxicity of a test agent is evaluated according to its ability to increase the release of RNA by the cells.

Another embodiment provides in vitro methods for identifying therapeutic agents. For example, cells or tissue cultures that are induced to undergo apoptosis (i.e., programmed cell death) may be treated with a test agent. If the level of released RNA of viable cells decreases over time, this would be an indication that the test agent inhibits the progression of apoptosis.

The invention also provides in vivo methods for evaluating the toxicity of an agent and to determine which organ or tissue is negatively affected by the agent. According to such methods, the blood of a subject is tested to determine the level of RNA specific for a particular tissue or cell type. The toxicity of the agent is evaluated based upon its ability to cause the cellular release of RNA as measured in the blood of the test subject. Such methods would be useful as in vivo assays for the evaluation of the toxicity of test agents, using, for example, test animals. The methods may also be used clinically to non-invasively monitor patients following drug treatment as an early warning of possible toxicity.

The present invention further provides non-invasive diagnostic methods for detecting tissue or organ damage. Such methods are useful in the clinical setting for the identification or diagnosis of disease and other pathologic conditions. The methods may also be used to track the progress of disease. According to such methods, the blood of a subject is tested for the presence of a tissue-type specific RNA. An increase in the level of RNA over time for a specific tissue is indicative of disease exacerbation therein. Likewise, a decrease in RNA levels would indicate alleviation of the disease.

In addition, the present invention provides non-invasive diagnostic methods for evaluating the efficacy of therapeutic agents or methods in a subject. According to such methods, a return to normal RNA levels released by previously injured cells of a target tissue-type will indicate that a therapeutic agent is having its desired effect on the target tissue.

It will be appreciated by those with skill in the art based upon the present disclosure, that any viable animal cell or cell line may be used for toxicity evaluation of agents by the in vitro methods of this invention. For example, such cells may be mammalian, avian, reptilian, amphibian, piscinian or insect derived. It will be apparent to those with skill in the art that the cells for use in the methods of the invention will, preferably, bear a close resemblance to cells of the organism against which toxicity is being evaluated. For example, if an agent is being evaluated for possible toxicity in humans, it is preferable to test the agent using mammalian derived cells, more preferably, human derived cells. Furthermore, it will be apparent to those with skill in the art that cells derived from a particular tissue-type or organ will be preferable when evaluating toxicity of that tissue-type or organ. For example, if an agent is being evaluated for possible toxicity in the liver, it is preferable to test the agent using liver-derived cells.

The cells used in the in vitro methods may be derived from any of a number of organs and/or tissues of an animal. For example with respect to mammal cells, such cells may be derived from endothelium, thymus, spleen, bone marrow, lymphocytes, liver, kidney, heart, testis, ovary, heart and skeletal muscle.

Intact viable hepatocytes may be prepared, for example, from liver tissue of laboratory animals or donated human livers by methods known in the art, including those described in Maines et al. (1998). Hepatocytes may be prepared by a two-step collagenase digestion. In the first step, tissue is perfused with a buffer containing EGTA to deplete the tissue of interstitial calcium and to weaken epithelial cell-cell adhesion, in a second step, a second perfusion buffer is used containing collagenase, which digests intercellular collagen, eventually leading to the complete digestion of cell-cell contacts.

In a preferred embodiment utilizing a mammalian cell line, the cells are prepared prior to treatment with a test agent by developing a culture of the cells. As is well known by those with skill in the art, culture conditions will vary depending upon the cell types used. For example, when using a cell line, the cells are routinely allowed to grow until they reach a density of 50-100% confluency. Confluency is measured by visually estimating the number of cells that are in contact with each other. For example, if cells have reached a density where there is no space between them, this is considered 100% confluency.

As will be apparent to those with skill in the art based upon the present description, the desired density will depend upon many factors, including the types of cells and growing conditions used and treated with varying concentrations of the test agent. As those with skill in the art will appreciate based upon the present disclosure, for any given test agent the concentration range will vary depending upon the cell type and test agent used, but should be between zero and that concentration which results in cell death. The period of exposure will generally range from between about five minutes to about 48 hours, preferably about two hours to about 32 hours. As will be apparent to those with skill in the art based upon the present description, the optimal period of exposure will depend upon many factors, including the types of cells used and the physical and chemical characteristics of the test agent.

Additional methods and techniques for culturing mammalian cells are well known to those with skill in the art. General methods of cell culture preparation and handling are described in Bonfacino et al. (1998). See also Freshney, R. I. (1993).

In the practice of the in vitro methods of this invention, RNA release by cells is detected by methods known to those with skill in the art, based upon the present description. Generally, the detection of RNA involves a multi-step process which includes, extraction, amplification and detection, as described below.

The in vivo methods of the invention may be utilized with any vertebrate subject, including, for example, a mammalian, avian, reptilian, amphibian or piscinian subject. Preferably a mammalian subject is used, including, for example a dog, cat, bovine, horse, rabbit, mouse, rat or primate.

In the practice of the in vivo methods of this invention, blood is drawn from a subject by standard methods known to those with skill in the art, into a collection tube, preferably siliconized glass, either with or without anticoagulants. For the preparation of plasma, blood is preferably stored with EDTA, sodium citrate, heparin, or similar anticoagulants. Preferably, blood is collected into tubes containing EDTA and stored unfractionated at 4° C. Alternatively, unprocessed clotted blood without anticoagulant for preparation of serum should be stored at 4° C. and processed within six hours. Regardless of method used, blood is best processed for analysis of RNA content as soon as possible, preferably within six hours so as to avoid degradation or additional release of RNA, thereby affecting the accuracy of the results.

For long-term storage, plasma or serum is preferably fractionated from whole blood and then frozen. This reduces the possibility of extraneous intracellular RNA released from the lysis of frozen and thawed cells, or, with respect to the use of PCR amplification, the release of inhibitors to PCR such as porphyrins and hematin, which might reduce the sensitivity of quantification of RNA. Plasma or serum may be fractionated from whole blood by centrifugation, using preferably gentle centrifugation at about 300 to 800 times gravity for about five to ten minutes, or fractionated by other standard methods. Since heparin may interfere with RT-PCR, use of heparinized blood may require deactivation of heparinase by methods known to those skilled in the art.

Generally, the detection of RNA for the practice of the in vitro and in vivo methods of this invention entails a multi-step process: (1) extraction of RNA; (2) amplification, which may involve reverse transcription of RNA to its cDNA; and (3) detection. While not intended as a commitment to any particular theory or mechanism, it is believed that extracellular RNA is present extracellularly as protein-RNA, lipoproteln-RNA complexes, lipid-RNA or DNA-RNA complex, and that such complexing may interfere with amplification and detection of RNA levels. Hence, it is preferable according to this theory to use an extraction step in order to dissociate the RNA from its associated complexes, prior to amplification and detection.

Any of a number of nucleic acid extraction methods known to those with skill in the art may be used in the practice of the invention. Although many of the published methods are intended for extraction of intracellular RNA, they may be used as described in the literature or with modification that will be apparent to those with skill in the art, based on the present disclosure. For example, extracellular RNA may be extracted using silica particles, glass beads, or diatoms, as in methods described in Boom et al (1990) or Cheung et al. (1994).

in an exemplary method for extracting RNA from cell growth media for the in vitro methods of the invention, the media that has been separated from the cells by methods well known in the art (for example, by centrifugation or filtration) are treated with an RNA stabilizing agents, such as a chaotropic substance, for example, guanidimium (iso)thiocyanate as described in U.S. Pat. No. 5,234,809. The RNA is then bound to a solid binding agent, such as silica particles. The RNA-solid phase may then be separated from the liquid phase by filtration. The RNA may then be eluted from the silica particles using the RNA may be eluted using a buffer consisting of 10 mM Tris-HCl, one mM EDTA (pH 8.0).

In an exemplary extraction method from blood, about 100 to 250 ml of cell free plasma or serum are mixed with 40 microliters of an aqueous silica suspension, prepared as described below, and about 900 microliters of lysis buffer, prepared as described as described below, and mixed at room temperature for about 10 minutes. The mixture is then centrifuged at 12,000×g for one minute and the supernatant is removed. The resulting silica-RNA pellet is then washed twice with about 450 microliters of a washing buffer, prepared as described below, followed by about one ml of 70% (vol/vol) ethanol. Finally, the pellet is wash with one mi (vol/vol) acetone and dried at about degrees 56° C. for about 10 minutes. RNA is then eluted from the silica pellet by suspending in about 20 to 50 microliters of diethyl procarbonate-treated water at 56° C. for about 10 minutes followed by centrifugation at about 12,000 times gravity for about three minutes. Alternatively, the RNA may be eluted using a buffer consisting of 10 mM Tris-HCl, one mM EDTA (pH 8.0) and an RNase inhibitor (e.g., RNAsin®, Promega, Madison Wis.), with or without a proteinase, such as proteinase K, according to the method described in Boom et al. (1991). The resulting RNA containing supernatant is recovered for amplification and detection.

Prior to amplification and detection, if may be desirable to further purify the RNA by removal of trace DNA. Further purification may be accomplished using DNase according to methods described in Rashtchian, A. (1994).

The aqueous silica suspension described above may be prepared by suspending 60 grams of silicon dioxide (Sigma-Aldrich Corp., St. Louis, Mo.) in 500 ml of demineralized sterile double-distilled water. The suspension is then allowed to settle for about 24 hours at room temperature. The supernatant is removed and the particles are resuspended in demineralized, sterile double-distilled water added to equal a volume of 500 milliliters. Once the suspension has settled, about 440 milliliters of the supernatant is removed and the the pH of the suspension is adjusted to about and pH 2 using hydrochloric acid.

The lysis buffer described above is prepared by dissolving 120 grams of guinidine thiocyanate into 100 ml of 0.1 M Tris hydrochloride (Tris-HCl) (pH 6.4), and 22 milliliters of 0.2 M EDTA, adjusted to pH 8.0 with NaOH, and 2.6 grams of Triton X-100 (Sigma-Aldrich Corp.).

The washing buffer described above is prepared by dissolving 120 grams of guinidine thiocyanate into 100 milliliters of 0.1 M Tris-HCl (pH 6.4).

In a preferred method of RNA extraction from blood, a PAXgene™ Blood RNA kit (cat. no. 762132, Qiagen Inc., Valencia, Calif.) is used to extract RNA using a silica-gel-membrane system, in this method, blood samples are centrifuged to pellet nucleic acids and the pallet is washed and treated with proteinase K. Ethanol is added and the sample is applied to a spin column containing an RNA selectively binding silica-gel membrane. Following centrifugation to remove impurities, the RNA is eluted with an optimized buffer, In a preferred method of RNA extraction from the supernatants derived from the in vitro methods of this invention, an RNeasy™ kit (cat. no. 74124, Qiagen Inc., Valencia, Calif.) is used to extract RNA using a silica-gel-membrane system similar to the PAXgene™ Blood RNA kit described above.

Alternative methods may be used to extract RNA, including but not limited to centrifugation through a cesium chloride gradient, for example, as described by Chirgwin et al. (1979), and co-precipitation of extracellular RNA from plasma or serum with gelatin, for example, as generally described in Fournie et al. (1986). Other methods of RNA extraction will be apparent to those skilled in the art based upon the present disclosure.

RNA which has been extracted, as described above, may be amplified using a nucleic acid amplification assay. Any nucleic acid amplification assay capable of permitting detection of small numbers of RNA molecules may be used in the practice of the invention. Applicable assays include, but are not limited to, reverse transcriptase polymerase chain reaction (RT-PCR), ligase chain reaction (see, for example, Abravaya, K. et al. (1995), branched DNA signal amplification (see, for example, Jrdea, M. S. et al. (1993)), isothermal nucleic acid sequence based amplification (NASBA) (see, for example, Kievits, T. et al. (1991)), and other self-sustained sequence replication assays.

The preferred embodiment for amplification of RNA for this invention is through the use of RT-PCR. Methods for amplification of RNA using RT-PCR are well known to those with skill in the art and are well described in the literature (see, for example, Ausubel et al. (1994) and Innis et al. (1990)).

The choice of primers that are to be used for amplification and probes for detection of the amplification product, for example, by RT-PCR, will depend upon the types of cells that are evaluated through the methods of the invention. For the in vitro methods of this invention, such evaluation involves the use of cell cultures comprising one or more cell types. For the in vivo methods, the evaluation may involve a large number of different cell types within the body of a subject.

Accordingly, sets of probes and primers should target one or more transcribed genes of such cells such that the transcription thereof may be used to identify those cells. Preferably, such probes and primers will target RNAs that are unique to the particular cells-type, it is also preferable that such genes be transcribed at a relatively high level, and preferably continuously, regardless of the state of the cell or conditions affecting the cell.

Any suitable transcribed gene may be used to construct such probes and primers. For example, for targeting the liver, the albumin gene may be used. Representative albumin gene sequences include accession numbers; V01222.1 (rat); BC034026.1 (human); P02769.4 (bovine); CAB64867.1 (canine); P19121.2 (chicken); X78598.1 and O91134 (cobra); P49064.1 and X84842.1 (feline); P08759.2, P14872.2, P21847.1 and AA D09358.1 (frog); O35090.1 (gerbil); X74045.1 (horse); P07724.3 (mouse); M36787.1 (pig); P49065.2 (rabbit); O28522.1 and M90463.1 (rhesus monkey); AAL56646.1 (salamander); P21848.1 and O03156.1 (salmon); and X17055.1 (sheep).

For targeting the heart, the troponin T gene may be used Representative troponin T gene sequences include accession numbers: BC161855.1 (rat); X83743.1 (human); AB085600.1 (bovine); U84037.1 (brown trout); AY005140.1 (canine); K02263.1 (chicken); AF020946.1 (mouse); and L40178.1 (rabbit)

An alternative gene that may be used for targeting the heart is cardiac actin. Representative cardiac actin gene sequences include accession numbers; X80130.1 (rat); and r J00071.1 (human).

For targeting the smooth muscle, the SM22 gene may be used. Representative SM22 gene sequences include accession numbers; M83107.1 (rat); D17409.1 (human); M83105.1 (chicken); Z68618.1 (mouse): and AF053829.1 (pig).

An alternative gene that may be used for targeting the smooth muscle is smooth muscle actin. Representative smooth muscle actin gene sequences include accession numbers: J02781.1 (rat); and BC017554.2 (human, SEQ ID NO:7).

For targeting the kidney, the Tamm-Horsfall protein gene may be used. Representative Tamm-Horsfall protein gene sequences include accession numbers: M63510.1 (rat); and M15881.1 (human).

An alternative gene that may be used for targeting the kidney is aquaporin-2. Representative aquaporin-2 gene sequences include gene accession numbers: P34080.1 (rat); AF147093.2 (human); AF028005.1 (bovine); AY055468.1 (mouse); and AF050152.1 (sheep).

Yet another alternative gene that may be used for targeting the kidney is the kidney androgen specific protein. A representative kidney androgen specific protein gene sequence is accession number U25808.1 (rat).

The above-mentioned genes are for illustrative purposes only. These lists are not intended to include all target genes for given tissue or cell types. Other suitable gene targets will be apparent to those with skill in the art based upon the present disclosure.

Methods for preparing and using probes and primers are well known in the art, and are described, for example, in Sambrook et al. (1989), Ausubel et al. (1994) and Innis et al. (1990), PCR primer pairs can be derived from known sequences, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO® version 6 software (Molecular Biology Insights, Inc. Cascade, Colo., oligo.net) is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas, South West Medical Center, Dallas Tex., genome.o-u.edu/pub/programs/primou.src.tar) is capable of choosing specific primers from megabase sequences and is thus useful for designing primers on a genome-wide scope. The Primer3, version 0.9, primer selection program (available to the public from the Whitehead Institute/MIT Center for Genome Research, Cambridge, Mass., genome.wi.mit.edu/genome_software/other/primer3.html) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Center, Cambridge UK, hgmp.mrc.ac.uk/Registered/Option/primegen.html) designs primers based on multiple sequence alignments, thereby allowing selection of primers that hybridize to either the most conserved or feast conserved regions of aligned nucleic acid sequences. Hence, this program is useful for identification of both unique and conserved oligonucleotides and polynucleotide fragments. Other oligonucleotide selection methods will be apparent to those with skill in the art based upon the present description.

RNA that has been extracted and/or amplified, as described above, may be detected using a detection method. Methods of RNA detection are well known by those with skill in the art, and are described, for example, in Sambrook et al. (1989), Ausubel et al. (1994) and Innis et al. (1990).

A preferred detection system uses real-time detection of RNA during PCR cycles using an integrated thermal cycler, a fluorescence inducing light source and detector. An exemplary instrument to perform such detection is the ABI PRISM® 7700 Sequence Detection System (Applied Biosystems, Foster City, Calif.).

Alternative methods for defection of RNA will be apparent to those with skill in the art based upon the present description. Such methods may include, for example, gel electrophoresis followed by southern blot analysis (see, for example, Nguyen, T. D. (1989)), ELISA detection methods (see, for example, Landgraf, A. et al. (1991), Coutlee, F. et al. (1989) and Bobo, L. et al. (1990)) and methods using electrochemiluminescence detection (see, for example, Blackburn, G. F. (1991) and DiCesare, J. et al. (1993)). Electrophoresis detection methods may involve a comparison of bands of two or more RNA populations. Bands present on an autoradiograph of one gel from one RNA population, and not present on another, correspond to the presence of a particular RNA in one population and not in the other, and thus indicate a gene that is likely to be differentially expressed (see, for example, Williams, J. G. (1990), Welsh, J. et al. (1990), Woodward, S. R. (1992), Nadeau, J. H. (1992), Liang, P. et al. (1992), Welsh, J. et al. (1992) and Liang. P. et al. (1993)).

Finally, detection methods for the present invention may involve the use of arrays or microarrays. Arrays and microarrays are sets of distinct polynucleotides or oligonucleotides synthesized on a substrate, such as paper, nylon or other type of membrane, filter, chip, glass slide, or any other suitable solid support. In a preferred embodiment, arrays and microarrays may be prepared and used according to the methods described in U.S. Pat. No. 5,837,832, PCT Patent Application Publication Number WO 95/11995, Lockhart et al. (1996) and Schena, M. et al. (1996). In other embodiments, such arrays are produced by the methods described in U.S. Pat. No. 5,807,522.

The disclosures of alt patents, applications, and gene accession numbers (including associated information), publications, and documents, for example brochures or technical bulletins, cited herein, are hereby expressly incorporated by reference in their entirety.

It is believed that one skilled in the art can, using the present description, including the examples, drawings, sequence listings and attendant claims, utilize the present invention to its fullest extent. The following Examples are to be construed as merely illustrative of the practice of the invention and not limitative of the remainder of the disclosure in any manner whatsoever.

EXAMPLES

Example 1

In Vitro Assay of $H_2O_2$ Induced Cell Damage Using Rat Endothelial Cells as Measured by Release of Beta Actin mRNA Versus LDH Immortalized rat endothelial cells (Catalog No. CRL-2222, ATCC, Manassas, Va.) were grown in Vitacell® Dulbecco's MEM (Catalogue No. 30-2002, ATCC) supplemented with 64.8 mg/dl heparin (Catalogue No. H3393, Sigma-Aldrich Corp., St. Louis, Mo.) and 5% Gibco™ FBS (Invitrogen Corporation, Carlsbad, Calif.) until approximately 80% confluency was reached. The medium was removed from the cells and replaced with MEM without supplement. Cells were incubated with $H_2O_2$ at final concentrations of 0.0003%, 0.003%, 0.01%, 0.03%, and 0.1% for four hours. Control cells were treated only with 10× stock PBS (pH 7.4) (Invitrogen Corporation). At the end of the treatment period, supernatant was removed and centrifuged at 16,000 RPM at room temperature. The resulting supernatant was separated from the cells and cell debris. The supernatant was analyzed by LDH analysis, to measure membrane integrity as a function of the amount of LDH released (see, Maines et al. (1998); Putnam et al. (2002)). LDH analysis was performed according to manufacturer's instructions using an automated Boehringer Mannheim/Hitachi 917 Analyzer (Roche Diagnostics Corporation, Indianapolis, Ind.). A portion of the supernatant (650 µl) was also used for RNA extraction using the RNsasy™ mini kit (Qiagen Inc., Valencia, Calif.) according to manufacturer instructions. The supernatant was analyzed using RT-PCR for presence of rat beta actin specific mRNA (accession numbers V01217 and J00691) using 5'-AGAGGGAAATCGTGCGTGAC-3' as the forward primer. 5'-ATGCCACAGATTCCATACCA-3' as the backward primer and 5'-CACTGCCGCATCCTCTTCCTCCC-3' as the probe. RT-PCR was performed on a ABI PRISM® 7700 Sequence Detection System (Applied Biosystem). Reactions without template served as negative control and rat endothelial cell RNA (100 ng/µl) serve as a positive control.

The results of this Example 1 appear in Table 1 below. Table 1 shows that cell damage is detectable at much lower concentrations of $H_2O_2$ based upon the level of released beta actin mRNA than by the level of LDH.

TABLE 1

Comparison of LDH Assay to Beta Actin mRNA RT-PCR Assay

| $H_2O_2$ concentration (%) | LDH (U/I) | PCR Cycles | Fold over control* |
|---|---|---|---|
| PBS control | <5 | 40 | 1 |
| 0.0003 | <5 | 38.56 | 2.5x |
| 0.003 | <5 | 39.12 | 2x |
| 0.01 | <5 | 37.45 | 6x |
| 0.03 | 5 | 32.05 | 247x |
| 0.1 | 16 | 30.78 | 596x |

*Each PCR cycle is equivalent to a two-fold amplification of mRNA.

Example 1 illustrates the in vitro methods of this invention for evaluating the cell damaging effect of an agent on a subject. Furthermore, Example 1 shows the advantage of the methods of this invention over traditional methods for evaluating the cell damaging effect of an agent as measured by LDH release.

Example 2

In Vivo Assay of $H_2O_2$ Induced Cell Damage Using Rat Endothelial Cells as Measured by Release of Beta Actin mRNA Four male Sprague_Dawley/Crl:CD® (SD)IGS BR rats (Charles River Laboratories, Wilmington, Mass.) having a weight of between 250-450 g were orally administered (by gavage) 1400 mg/kg of acetaminophen (Sigma-Aldrich Corp.) in 0.5% methylcellulose vehicle. Four control rats were administered a quantity of methylcellulose vehicle (no acetaminophen) having a volume approximately equal to that received by treated rats. After 24 hours, all rats were euthanized and livers were collected by necropsy. At necropsy, blood samples were collected via the vena cava (approximately 0.5 ml) in microtainer tubes. All livers were then fixed in 10% neutral buffered formalin and processed for histopathology by trimming trimmed, dehydrating, embedding in paraffin, sectioning, mounting on glass slides, and staining with hematoxylin and eosin stains.

The blood was analyzed for hepatocyte damage markers (ALT, AST and 5'NT) according to manufacturers instructions using an automated Boehringer Mannheim/Hitachi 917 analyzer (Roche Diagnostics Corporation, Indianapolis, Ind.) (see, Duncan, J. R. et al. (1994)).

For RNA extraction, approximately 2.5 ml of blood per rat was collected in PAXgene™ Blood RNA tubes (Qiagen Inc., Valencia, Calif.). RNA was extracted according manufacturer instructions provided with the PAXgene™ Blood RNA kit. The extracted RNA using RT-PCR to measure the level of albumin (accession numbers V01222 and J00698) using a first primer set having 5'-AGAAGCTTGGAGAGTATGGAT-TCC-3' as the forward primer, 5'-CTTGCTGCCTCCAC-GAGAGT-3' as the backward primer and 5'-TTCGATACAC-CCAGAAAGCACCTCAGGT-3' as the probe. RT-PCR was performed on a ASI PRISM® 7700 Sequence Detection System (Applied Biosystems, Foster City, Calif.).

The results appear in Table 2 below. Table 2 shows that cell damage is detectable with a higher level of sensitivity by measuring albumin RNA in blood as compared to ALT, AST and 5'NT markers for hepatocyte damage. Histopathological analysis of rats indicated moderate levels of damage. Microscopically, there was a moderate centrilobular degeneration which was multifocal in two of the animals and was characterized by hepatocellular degeneration and necrosis, edema fluid, hemorrhages, and infiltration of mononuclear cells and occasional neutrophils in the other two animals. The severity and distribution of the microscopic lesions correlated well with the measured increases in ALT, AST, 5'NT, and albumin RT-PCR.

TABLE 2

| Animal | Hepatocellular Degeneration | ALT (U/L)* | AST (U/l)* | 5'NT (U/L)* | RT-PCR** |
|---|---|---|---|---|---|
| 1 | Diffuse | 134x | 109x | 3x | 362x |
| 2 | Diffuse | 122x | 139x | 3x | 294x |
| 3 | Multifocal | 18x | 31x | 2x | 90x |
| 4 | Multifocal | 18x | 28x | 2x | 24x |

*Fold changes over mean control values.
**Fold change over mean control values calculated assuming a two-fold amplification of mRNA during each cycle, Example 2 illustrates the in vivo methods of this invention for evaluating the cell damaging effect of an agent using hepatocytes. Furthermore, Example 2 shows the advantage of the methods of this invention over traditional methods that measure ALT, AST and 5'NT markers of heptocyte damage.

REFERENCES

Abravaya, K. et al. (1995) Nucleic Acids Research 23, 675-682; Ausubel et al. (1994) Current Protocols in Molecular Biology, John Wiley & Sons, Hoboken, N.J.; Blackburn, G. F. (1991) et al. Olin Chem 37, 1534-1539; Bobo, L. et al. (1990) J. din Micra 28, 1968-1973; Boom, R. et al. (1990) J. Clin. Microbiology 28, 495-503; Boom, R. et al. (1991) J. Clin. Microbiology 29, 180-1811; Bonfacino et al. (1998) Current Protocols in Cell Biology, John Wiley & Sons, Inc., Hoboken, N.J.; Chen, X. Q. et al. (2000) Clin. Cancer Res. 6, 3823-3826; Cheung et al. (1994) J Clin. Microbiology 32, 2593-2597; Chirgwin, J. M. et al. (1979) Biochemistry 18, 5294-5299; Coutlee, F. et al. (1989) Analytical Biochemistry 181, 96-105; DiCesare, J. et al. (1993) BioTechniques 15, 152-157; Fournie, G. J. et al. (1988) Analytical Biochemistry 158, 250-256; Diehn, M. et al. (1993) Nat. Genet. 25, 58-62; Duncan, J. R. et al. (1994) Veterinary Laboratory Medicine, Clinical Pathology. Third edition. Iowa State Press, Ames, Iowa; Freshney, R. I. (1993) Culture of Animal Cells. A Manual of Basic Techniques, 3rd ed. Wiley-Liss, New York, N.Y.; Hasselmann, D. O. (2001) Clin. Chem. 47, 1488-1489; Hayward R. E. et al. (1993) Mol. Microbiol. 35, 6-14; Innis et al. (1990) PCR Protocols, A Guide to Methods and Applications, Academic Press, San Diego Calif.; Jrdea, M. S. et al. (1993) AIDS 7 (supp. 2), $11-514; Johannes G. et al. (1993) Proc. Natl. Acad. Sci. USA 96, 13118-23; Kievits, T. et al. (1991), J. Virological. Methods 35, 273-286; Kopreski, M. et al. (1999) Clin. Cancer Res. 5, 1961-1965; Landgraf, A. et al. (1991) Analytical Biochemistry 198, 86-91; Liang, P. et al., (1992) Science 287, 967; Liang, P. et al. (1993) Nucl. Acids Res. 3269; Lo, K. W. et al. (1999) Clin. Chem. 45, 1292-1294; Lockhart et al. (1996) Nat. Biotech. 14, 1675-1680; Mandel and Metais (1948) C.R. Acad. Sci. Paris 142, 241-243; Maines et al. (1998) Current Protocols in Toxicology, John Wiley & Sons, Inc., Hoboken, N.J.; Nadeau, J. H. (1992) Mamm. Genome 3, 55; Nguyen, T. D. (1989) BioTechniques 7, 238-240; Ng, E. K. O. (2002) Clin. Chem. 48, 1212-1217; Poon, L. L. et al. (2000) Clin. Chem. 46, 1832-1834; Putnam, K. P. et al. (2002) Toxicol. In Vitro 18, 599-607; Rashtchian, A. (1994) PCR Methods Applic. 4, S83-S91; Sambrook et al. (1989) Molecular Cloning: A Laboratory Manual, Cold Spring Harbor Press, Plainview N.Y.; Schena, M. et al. (1996) Proc. Natl. Acad. Sci. 93, 10614-10619; Scherf, U. et al. (1993) Nat. Genet. 24, 236-44; Schmidt, D. M. and Ernst, J. D. (1995) Anal. Biochem. 232, 144-146; Tsui, N.Y. B. (2002) Clin. Chem. 48, 1647-1653; Welsh, J. et al., (1990) Nucl. Acids Res., 18, 7213; Welsh, J. et al. (1992) Nucl. Acid Res. 20, 4965; Williams, J. G. (1990) Nucl. Acids Res. 18, 6531; Woodward, S. R., (1992) Mamm. Genome, 3, 73.

The invention claimed is:

1. A method for evaluating whether an agent causes cell damage comprising: treating one or more cells with an agent in vitro; and measuring the effect of said agent on the amount of RNA released by said cells, wherein the RNA released by cells comprise RNA markers comprising mRNA for one or more proteins, and where a protein is selected from the group consisting of albumin, troponin T, cardiac actin, smooth muscle actin, Tamm-Horsfall protein, kidney androgen specific protein, and Aquaporin-2.

2. A method of claim 1 wherein said cells comprise one or more cells of mammalian origin.

3. A method of claim 2 wherein said cells comprise one or more cells of human origin.

4. A method of claim 1 wherein said measurement comprises measuring the effect of said agent on the quantity of one or more RNA markers released by said cells.

5. A method of claim 4 wherein said cells are of mammalian liver origin and said one or more RNA markers comprise mRNA for albumin.

6. A method of claim 4 wherein said cells are of mammalian heart origin and said one or more RNA markers comprise mRNA for one or more of troponin T and cardiac actin.

7. A method of claim 4 wherein said cells are of mammalian smooth muscle origin and said one or more RNA markers comprise mRNA for one or more of SM22 and smooth muscle actin.

8. A method of claim 4 wherein said cells are of mammalian kidney origin and said one or more RNA markers comprise mRNA for one or more of Tamm-Horsfall protein and Aquaporin-2.

9. A method of claim 1 further comprising characterizing said agent as an agent that is likely to cause cell injury, wherein said injury is characterized by increased RNA release as compared to RNA released from cells lacking treatment with the agent, provided the amount of RNA released by said cells has increased by at least two fold.

10. A method of claim 4 wherein said measurement comprises measuring RNA release by RT-PCR.

* * * * *

UNITED STATES PATENT AND TRADEMARK OFFICE
CERTIFICATE OF CORRECTION

| | | |
|---|---|---|
| PATENT NO. | : 7,968,291 B2 | Page 1 of 1 |
| APPLICATION NO. | : 11/960093 | |
| DATED | : June 28, 2011 | |
| INVENTOR(S) | : Brees et al. | |

It is certified that error appears in the above-identified patent and that said Letters Patent is hereby corrected as shown below:

Column 3, Line 16: correct "ID NO3" to read -- ID NO:3 --

Column 7, Line 51: correct first words of paragraph "in an exemplary"
   to read -- In an exemplary --

Column 12, Line 10: correct "RNsasy™"
   to read -- RNeasy™ --

Column 13, Table 2: correct table column "AST (U/l)*" to read -- AST (U/L)* --

Column 14, Line 12, Fournie: correct "(1988)" to read -- (1986) --
   Line 23, Jrdea: correct "$11" to read -- S11 --

Signed and Sealed this
Sixth Day of December, 2011

David J. Kappos
*Director of the United States Patent and Trademark Office*

SEQUENCE LISTING

<160> NUMBER OF SEQ ID NOS: 7

<210> SEQ ID NO 1
<211> LENGTH: 2059
<212> TYPE: DNA
<213> ORGANISM: Homo sapiens

<400> SEQUENCE: 1

```
agcttttctc ttctgtcaac cccacacgcc tttggcacaa tgaagtgggt aacctttatt      60
tcccttcttt ttctctttag ctcggcttat tccaggggtg tgtttcgtcg agatgcacac     120
aagagtgagg ttgctcatcg gtttaaagat ttgggagaag aaaatttcaa agccttggtg     180
ttgattgcct ttgctcagta tcttcagcag tgtccatttg aagatcatgt aaaattagtg     240
```

| | |
|---|---|
| aatgaagtaa ctgaatttgc aaaaacatgt gttgctgatg agtcagctga aaattgtgac | 300 |
| aaatcacttc atacccttt tggagacaat tatgcacagt tgcaactctt cgtgaaacct | 360 |
| atggtgaaat ggctgactgc tgtgcaaaac aagaacctga gagaaatgaa tgcttcttgc | 420 |
| aacacaaaga tgcaaaccca aacctccccc gattggtgag accagaggtt gatgtgatgt | 480 |
| gcactgcttt tcatgacaat gaagagacat ttttgaaaaa atacttatat gaaattgcca | 540 |
| gaagacatcc ttacttttat gccccggaac tccttttctt tgctaaaagg tataaagctg | 600 |
| cttttacaga atgttgccaa gctgctgata aagctgcctg cctgttgcca aagctcgatg | 660 |
| aacttcggga tgaagggaag gcttcgtctg ccaaacagag actcaagtgt gccagtctcc | 720 |
| aaaaatttgg agaaagagct ttcaaagcat gggcagtagc tcgcctgagc cagagatttc | 780 |
| ccaaagctga gtttgcagaa gttccaagt tagtgacaga tcttaccaaa gtccacacgg | 840 |
| aatgctgcca tggagatctg cttgaatgtg ctgatgacag gcggaccctt gccaagtata | 900 |
| tctgtgaaaa tcaagattcg atctccagta aactgaagga atgctgtgaa aaacctctgt | 960 |
| tggaaaaatc ccactgcatt gccgaagtgg aaaatgatga gatgcctgct gacttgcctt | 1020 |
| cattagctgc tgattttgtt gaaagtaagg atgtttgcaa aaactatgct gaggcaaagg | 1080 |
| atgtcttcct gggcatgttt ttgtatgaat atgcaagaag gcatcctgat tactctgtcg | 1140 |
| tgctgctgct gagacttgcc aagacatatg aaaccactct agagaagtgc tgtgccgctg | 1200 |
| cagatcctca tgaatgctat gccaaagtgt tcgatgaatt taaacctctt gtggaagagc | 1260 |
| ctcagaattt aatcaaacaa aattgtgagc ttttgagca gcttggagag tacaaattcc | 1320 |
| agaatgcgct attagttcgt tacaccaaga aagtaccca agtgtcaact ccaactcttg | 1380 |
| tagaggtctc aagaaaccta ggaaaagtgg gcagcaaatg ttgtaaacat cttgaagcaa | 1440 |
| aaagaatgcc ctgtgcagaa gactatctat ccgtggtcct gaaccagtta tgtgtgttgc | 1500 |
| atgagaaaac gccagtaagt gacagagtca ccaaatgctg cacagaatcc ttggtgaaca | 1560 |
| ggcgaccatg ctttcagct ctggaagtcg atgaaacata cgttcccaaa gagtttaatg | 1620 |
| ctgaaacatt caccttccat gcagatatat gcacactttc tgagaaggag agacaaatca | 1680 |
| agaaacaaac tgcacttgtt gagcttgtga acacaagcc caaggcaaca aaagagcaac | 1740 |
| tgaaagctgt tatggatgat ttcgcagctt ttgtagagaa gtgctgcaag gctgacgata | 1800 |
| aggagacctg ctttgccgag gagggtaaaa aacttgttgc tgcaagtcaa gctgccttag | 1860 |
| gcttataaca tcacatttaa aagcatctca gcctaccatg agaataagag aaagaaaatg | 1920 |
| aagatcaaaa gcttattcat ctgtttttct ttttcgttgg tgtaaagcca acaccctgtc | 1980 |
| taaaaaacat aaatttcttt aatcatttg cctcttttct ctgtgcttca aaaaaaaaa | 2040 |
| aaaaaaaaaa aaaaaaaaa | 2059 |

<210> SEQ ID NO 2
<211> LENGTH: 2002
<212> TYPE: DNA
<213> ORGANISM: Homo sapiens

<400> SEQUENCE: 2

| | |
|---|---|
| ccccaatcta atgggctaca gagtcagttt tgctacctct ggcgggggga ccatgggcat | 60 |
| cctgggggat caggggctgc ctttgggcca gggcccagga agaagggatc agtcgttgca | 120 |
| gctaagggcg tctggcaagc ccaggtgttc cggctcccag cccagaggcc ccctggtgcc | 180 |
| tcgactgcag gtgacagga agatggagcc agagaggaaa gtgggctcag tgttcccta | 240 |
| cccgcctctt ctctgtcccc agctcagcaa cagcacgacg gctggccagg cggtgactgt | 300 |

```
ggagctcttc ctgacactgc agctggtgct ctgcatcttc gcctccaccg atgagcgccg      360
cggagagaac ccgggcaccc ctgctctctc cataggcttc tccgtggccc tgggccacct      420
ccttggggta ggtcatggcc atgggttcca gcctccctgg agaaacagac acacagacca      480
ctccagagac agacacagag accccaagag ggacacatac acagaactct caagaggaac      540
agacacccca gaggtttgac tcctagatac ccagaggaca gatatcactc cagcccatct      600
gtaaataaaa cgtgatgtta attgtccatc acgtgggttc cctttaggct gaggtcaagc      660
actgcaggtg cgggacaagg acttcctgcc ctgtcctcac ctcccttctc tctttgatgc      720
cctcctccca ctgcagatcc attacaccgg ctgctctatg aatcctgccc gctccctggc      780
tccagctgtc gtcactggca aatttgatga ccactgggta atggctgaaa cccctgccc      840 tcccttctc tagaaaccca ttttagaggg agaacaagag ctggaatagc atgggatggg      900
ggctcagcag cggtacccca aaccctccac actcctcctg gtcctgggga gccttgggtt      960 ccaccctca gatctgatgc caaagactca gtttccatgt ctgtgaatga ggatgacaac     1020
agcttacctc actggcttct tgggaacagt aagtgaggtt accggtgtaa cccagataat     1080
gcagtgtctt ggcacttaga actctataag tgtgatattg acctatctgg tgccttagta     1140
tgtggtgagc ctgttctgag tgctttgcaa cattaactca gttttcacaa ccacccagga     1200
ggtagacatt ctttagagtg aaaggcacag agagggtaag taacttgtcg aagtgcacac     1260
agcacttaag tggtggaatc aggacacaca caggcagtgg cttcagaatt cgcacccta     1320 accccgcact gacaaggctt ccccagcagc tggcgttgtc gttgtaatta cataaataag     1380
cattttacta gattaatgtc ggggaggagg ggtgcggccg cagagtgtgc cgccggggcc     1440
tgagggctcc gcgtgccggt gcgggcgcgg gtgccaagcc gccctctccg ctcgccccca     1500
ggtcttctgg atcggacccc tggtgggcgc catcctgggc tccctcctct acaactacgt     1560
gctgtttccg ccagccaaga gcctgtcgga gcgcctggca gtgctgaagg gcctggagcc     1620
ggacaccgat tgggaggagc gcgaggtgcg acggcggcag tcggtggagc tgcactcgcc     1680
gcagagcctg ccacggggta ccaaggcctg agggccgcca gcggcctcta aggccccgac     1740
ggacgcttgt gaggcccgag gcagaagggc cacccccgtc cctcctctcc cgcaggtctg     1800
aagttggccc cccagcgcag agtagctgct tcctggacgt gcgcgcccag gccagtgctg     1860
tgagcaggcg gggaggaggc tgccggaggg agccctgagc ctggcaggtc ccctgccctg     1920
aggctgtgag cagctagtgg tggcttctcc agccttttc agggaactgg gaacttaggg     1980
gactgagctg gggagggagg ca                                             2002
```

<210> SEQ ID NO 3
<211> LENGTH: 1846
<212> TYPE: DNA
<213> ORGANISM: Homo sapiens

<400> SEQUENCE: 3

```
ggtatttaaa tatgttcctt gacttgggca gttagatata aatggacaag acactgatta       60
tattcctgac atggtgagag catgattttc tcattttttc ttctcatagg gagttatggt      120
gggtatgggt cagaaggact cctacgtagg tgatgaagcc cagagcaaga gaggcatcct      180
gaccctgaag tatcccatcg agcatggtat catcaccaac tggacgacga tggagaagat      240
ctggcaccac accttctaca atgagctccg tgttgctccc gaggagcacc ccaccctgct      300
cacagaggcc ccgctgaacc ccaaggccaa ccgggagaag atgactcaga tcatgtttga      360
gaccttcaat gtccctgcca tgtacgtggc catccaggca gtgctatccc tgtatgcttc      420
```

-continued

```
tggccgtacc acaggtatgc tgggctctgg ggacagttac tgatgaatca cattcccaag    480
tcaccgacct tgctgtgaat cagatccccc agttgaaaaa gggataatcc ctttcctccc    540
attccctagc aaggtctgtg ctaagagaaa gagttaacgg tagtgccctg aggttagttt    600
cggagcacaa ttattattgt tgagctgata gcttgtggag gtgggccttc cctcatttaa    660
agctcagcgc agtgtagcag cttggagtgc agcagtcatt gttatgtgtt taaaccatca    720
catcacctgg gcaagcatcc ccaaggagaa tacattccat acagggtctg actcaaaaga    780
gagagaaacg tgtaagttca ataggagcaa agaaaaacac ccttgggtgc ttacataatg    840
tggctgacaa gaaagatggt catttgaaag tgtcctcggg aattttttct actataatag    900
ttaaaaagat gagctgcagc ttgcttcaga tttagtattc ctgatgcgca ttttattct    960
ttgtgtgtaa ggaatctaat tttatctgga tcaatgccca ttgctagcat ctcttagcca   1020
agattggaag cgggctttgc cgtggctaga gcagtggtgt tgtcctcagg aatttacctt   1080
gttcttgtgt acttccccgg gcaggcattg ttctggactc tggggatggt gtaactcaca   1140
atgtccccat ctatgagggc tacgctttgc cccatgccat catgcgtctg gatctggctg   1200
gtcgggacct cactgactac ctcatgaaga tcctcactga gcgtggctac tcctttgtca   1260
ccactggtga gtgtgtgtgt ctcatctgcc acagtgtggg tctgctttcc tcctctctca   1320
ctgaatccgc ctacctccct ataattgact tcttgcttca gagcatgact gtgatactct   1380
ttatttctgt agctgaacgt gaaattgtcc gtgacattaa agagaagctg tgctatgtcg   1440
ccctggattt tgagaatgag atggccacag ctgcctcttc ctcctccttg gagaagagct   1500
atgaactgcc tgatggccaa gtcatcacta tcggcaatga gcgcttccgc tgtcctgaga   1560
cactcttcca gccctccttc attggtgagt tgtagggtct ggtgtagagg cacgattttc   1620
ctggaaatct tagggtctcc cagagtaaaa tctagaattc tcaagaagcc cttgagttaa   1680
aagaagtcat tgtttggatt cccacacagc tcaacctcaa gtcctgatgg ctcgattaaa   1740
ggggaagtct atgttctgct ctagtgatat aataaaggat gacacactga gttcatctca   1800
aaataaagga tgacacagag tagtaactga atagcactat ctgcag             1846
```

<210> SEQ ID NO 4
<211> LENGTH: 704
<212> TYPE: DNA
<213> ORGANISM: Rattus norvegicus

<400> SEQUENCE: 4

```
caaacgcctc cttgttcctc ttttgcctc catccagtca actgtggaaa gccaccctca     60
aggacagagt acaagaatgt ataaaagcct gggagaactc ttcctggact aattccttcc    120
tcctgctcac tggttgcctt aaccctactg aagcatgatg atctgcaagg tcctggtgat    180
cactgtcttc tgtgtgctga ctgtggcttt ccccagtttg gacatagatt caatcaatga    240
agaactacag gattcaatct ttgatatact aaactcaacc tctgacttcc aactggcatc    300
atatgaacca tcaacatctc ctccagagga tagcacatac caggaatcaa acactgactt    360
catgcaaacc acatattcca aaagcataca gatttctgag ctctctaatg gagctgagac    420
agtctcttcc agcttcctgg aagaagtcac tgagacttca gaaagcacag tggagttcc    480
attagctgag acaactacat tctcctctac ctccctgagaa gactttgaaa caagcctgtg    540
actaccattc tggatattga gtctttgtag aaaatcatgt aagtctaaga tgctcccagc    600
aaagaagaaa gaacaaggaa gtggtcctgg atgagaaatg ctgtgtcagg cacttatgag    660
ctctgcccctt acctttgtgg gcttaataaa taaatgttca tcgc                    704
```

<210> SEQ ID NO 5
<211> LENGTH: 1056
<212> TYPE: DNA
<213> ORGANISM: Homo sapiens

<400> SEQUENCE: 5

| | | | | | |
|---|---|---|---|---|---|
| tcttcactcc | ttcctgcgag | ccctgaggaa | gccttctttc | cccagacatg | gccaacaagg | 60 |
| gtccttccta | tggcatgagc | cgcgaagtgc | agtccaaaat | cgagaagaag | tatgacgagg | 120 |
| agctggagga | gcggctggtg | gagtggatca | tagtgcagtg | tggccctgat | gtgggccgcc | 180 |
| cagaccgtgg | gcgcttgggc | ttccaggtct | ggctgaagaa | tggcgtgatt | ctgagcaagc | 240 |
| tggtgaacag | cctgtaccct | gatggctcca | agccggtgaa | ggtgcccgag | aacccaccct | 300 |
| ccatggtctt | caagcagatg | gagcaggtgg | ctcagttcct | gaaggcggct | gaggactatg | 360 |
| gggtcatcaa | gactgacatg | ttccagactg | ttgaccttct | tgaaggcaaa | gacatggcag | 420 |
| cagtgcagag | gaccctgatg | gctttgggca | gcttggcagt | gaccaagaat | gatgggcact | 480 |
| accgtggaga | tcccaactgg | tttatgaaga | agcgcagga | gcataagagg | gaattcacag | 540 |
| agagccagct | gcaggaggga | aagcatgtca | ttggccttca | gatgggcagc | aacagagggg | 600 |
| cctcccaggc | cggcatgaca | ggctacggac | gacctcggca | gatcatcagt | tagagcggag | 660 |
| agggctagcc | ctgagcccgg | ccctccccca | gctccttggc | tgcagccatc | ccgcttagcc | 720 |
| tgcctcaccc | acaccgtgt | ggtaccttca | gccctggcca | agctttgagg | ctctgtcact | 780 |
| gagcaatggt | aactgcacct | gggcagctcc | tcctgtgcc | cccagcctca | gcccaacttc | 840 |
| ttacccgaaa | gcatcactgc | cttggcccct | ccctcccggc | tgcccccatc | acctctactg | 900 |
| tctcctccct | gggctaagca | ggggagaagc | gggctggggg | tagcctggat | gtgggccaag | 960 |
| tccactgtcc | tccttggcgg | caaaagccca | ttgaagaaga | accagcccag | cctgccccct | 1020 |
| atcttgtcct | ggaatatttt | tggggttgga | actctc | | | 1056 |

<210> SEQ ID NO 6
<211> LENGTH: 2353
<212> TYPE: DNA
<213> ORGANISM: Homo sapiens

<400> SEQUENCE: 6

| | | | | | |
|---|---|---|---|---|---|
| actaactcta | cctttctggc | ttcagggggga | ggagagttag | atcatgcatt | tgtccgatcc | 60 |
| atctctgttc | acaggacacc | agacatcaga | gacagagaga | aaaattcaaa | gggccaaccc | 120 |
| gtctttcctt | tgggcagtag | acctgaagta | gcgggaagac | cagaaaggat | ggggcagcca | 180 |
| tctctgactt | ggatgctgat | ggtggtggtg | gcctcttggt | tcatcacaac | tgcagccact | 240 |
| gacacctcag | aagcaagatg | gtgctctgaa | tgtcacagca | atgccacctg | cacgaggat | 300 |
| gaggccgtta | cgacgtgcac | ctgtcaggag | ggcttcaccg | gcgatggcct | gacctgcgtg | 360 |
| gacctggatg | agtgcgccat | tcctggagct | cacaactgct | ccgccaacag | cagctgcgta | 420 |
| aacacgccag | gctccttctc | ctgcgtctgc | cccgaaggct | tccgcctgtc | gcccggtctc | 480 |
| ggctgcacag | acgtggatga | gtgcgctgag | cctgggctta | gccactgcca | cgccctggcc | 540 |
| acatgtgtca | atgtggtggg | cagctacttg | tgcgtatgcc | ccgcgggcta | ccggggggat | 600 |
| ggatggcact | gtgagtgctc | cccgggctcc | tgcgggccgg | ggttggactg | cgtgcccgag | 660 |
| ggcgacgcgc | tcgtgtgcgc | ggatccgtgt | caggcgcacc | gcaccctgga | cgagtactgg | 720 |
| cgcagcaccg | agtacgggga | gggctacgcc | tgcgacacgg | acctgcgcgg | ctggtaccgc | 780 |
| ttcgtgggcc | agggcggtgc | gcgcatggcc | gagacctgcg | tgccagtcct | gcgctgcaac | 840 |

-continued

| | |
|---|---|
| acggccgccc ccatgtggct caatggcacg catccgtcca gcgacgaggg catcgtgagc | 900 |
| cgcaaggcct gcgcgcactg gagcggccac tgctgcctgt gggatgcgtc cgtccaggtg | 960 |
| aaggcctgtg ccggcggcta ctacgtctac aacctgacag cgcccccga gtgtcacctg | 1020 |
| gcgtactgca cagaccccag ctccgtggag gggacgtgtg aggagtgcag tatagacgag | 1080 |
| gactgcaaat cgaataatgg cagatggcac tgccagtgca acaggactt caacatcact | 1140 |
| gatatctccc tcctggagca caggctggaa tgtggggcca atgacatgaa ggtgtcgctg | 1200 |
| ggcaagtgcc agctgaagag tctgggcttc gacaaggtct tcatgtacct gagtgacagc | 1260 |
| cggtgctcgg gcttcaatga cagagacaac cgggactggg tgtctgtagt gaccccagcc | 1320 |
| cgggatggcc cctgtgggac agtgttgacg aggaatgaaa cccatgccac ttacagcaac | 1380 |
| accctctacc tggcagatga gatcatcatc cgtgacctca acatcaaaat caactttgca | 1440 |
| tgctcctacc ccctggacat gaaagtcagc ctgaagaccg ccctacagcc aatggtcagt | 1500 |
| gctctaaaca tcagagtggg cgggaccggc atgttcaccg tgcggatggc gctcttccag | 1560 |
| accccttcct acacgcagcc ctaccaaggc tcctccgtga cactgtccac tgaggctttt | 1620 |
| ctctacgtgg gcaccatgtt ggatgggggc gacctgtccc gatttgcact gctcatgacc | 1680 |
| aactgctatg ccacacccag tagcaatgcc acggaccccc tgaagtactt catcatccag | 1740 |
| gacagatgcc cacacactag agactcaact atccaagtgg tggagaatgg ggagtcctcc | 1800 |
| cagggccgat tttccgtcca gatgttccgg tttgctggaa actatgacct agtctacctg | 1860 |
| cactgtgaag tctatctctg tgacaccatg aatgaaaagt gcaagcctac ctgctctggg | 1920 |
| accagattcc gaagtgggag tgtcatagat caatcccgtg tcctgaactt gggtcccatc | 1980 |
| acacggaaag gtgtccaggc cacagtctca agggcttta gcagcttggg gctcctgaaa | 2040 |
| gtctggctgc ctctgcttct ctcggccacc ttgaccctga ctttcagtg actgacagcg | 2100 |
| gaaagccctg tgctccatgg ctgccatctc acctcctgct gggcaggggg catgatgcgg | 2160 |
| gccagtgctc cagccacaga aaagaaagtt catgctttgt tcagcctgcc ttcttttctc | 2220 |
| cctttaatc ctggctgtcg agaaacagcc tgtgtcttta aatgctgctt tttctcaaaa | 2280 |
| tgggacttgt gacggtgtac ctgaggcccc catctcctta aagagtgtgg caaaataatg | 2340 |
| attttaaat ctc | 2353 |

<210> SEQ ID NO 7
<211> LENGTH: 1426
<212> TYPE: DNA
<213> ORGANISM: Homo sapiens

<400> SEQUENCE: 7

| | |
|---|---|
| gtgtggagca gcccagccaa gcactgtcag gaatcctgtg aagcagctcc agctatgtgt | 60 |
| gaagaagagg acagcactgc cttggtgtgt gacaatggct ctgggctctg taaggccggc | 120 |
| tttgctgggg acgatgctcc cagggctgtt ttcccatcca ttgtgggacg tcccagacat | 180 |
| caggggtga tggtgggaat gggacaaaaa gacagctacg tgggtgacga agcacagagc | 240 |
| aaaagaggaa tcctgaccct gaagtacccg atagaacatg gcatcatcac caactgggac | 300 |
| gacatggaaa agatctggca ccactctttc tacaatgagc ttcgtgttgc ccctgaagag | 360 |
| catcccaccc tgctcacgga ggcacccctg aaccccaagg ccaaccggga gaaaatgact | 420 |
| caaattatgt ttgagacttt caatgtccca gccatgtatg tggctatcca ggcggtgctg | 480 |
| tctctctatg cctctggacg cacaactggc atcgtgctgg actctggaga tggtgtcacc | 540 |
| cacaatgtcc ccatctatga gggctatgcc ttgccccatg ccatcatgcg tctggatctg | 600 |

```
gctggccgag atctcactga ctacctcatg aagatcctga ctgagcgtgg ctattccttc        660
gttactactg ctgagcgtga gattgtccgg gacatcaagg agaaactgtg ttatgtagct        720
ctggactttg aaaatgagat ggccactgcc gcatcctcat cctcccttga gaagagttac        780
gagttgcctg atgggcaagt gatcaccatc ggaaatgaac gtttccgctg cccagagacc        840
ctgttccagc catccttcat cgggatggag tctgctggca tccatgaaac cacctacaac        900
agcatcatga agtgtgatat tgacatcagg aaggacctct atgctaacaa tgtcctatca        960
gggggcacca ctatgtaccc tggcattgcc gaccgaatgc agaaggagat cacggcccta       1020
gcacccagca ccatgaagat caagatcatt gcccctccgg agcgcaaata ctctgtctgg       1080
atcggtggct ccatcctggc ctctctgtcc accttccagc agatgtggat cagcaaacag       1140
gaatacgatg aagccgggcc ttccattgtc caccgcaaat gcttctaaaa cactttcctg       1200
ctcctctctg tctctagcac acaactgtga atgtcctgtg gaattatgcc ttcagttctt       1260
ttccaaatca ttcctagcca aagctctgac tcgttaccta tgtgtttttt aataaatctg       1320
aaataggaaa aaaaaaaaaa aaaaaaaaaa aaaaaaaaaa aaaaaaaaaa aaaaaaaaaa       1380
aaaaaaaaaa aaaaaaaaaa aaaaaaaaaa aaaaaaaaaa aaaaaa                     1426
```